United States Patent [19]

Mehrotra et al.

[11] Patent Number: 5,101,018

[45] Date of Patent: Mar. 31, 1992

[54] METHOD FOR RECOVERING RECOMBINANT PROTEINS

[75] Inventors: Vikram P. Mehrotra; Ray E. Barker, both of Terre Haute, Ind.

[73] Assignee: International Minerals & Chemical Corp., N.Y.

[21] Appl. No.: 364,846

[22] Filed: Jun. 12, 1989

[51] Int. Cl.$^5$ .............................. C07K 3/24
[52] U.S. Cl. ................... 530/399; 530/419; 530/421
[58] Field of Search ............ 530/350, 351, 399, 419, 530/421

[56] References Cited

U.S. PATENT DOCUMENTS

| | | | |
|---|---|---|---|
| 2,175,090 | 10/1939 | Parfentjev | 435/269 |
| 3,657,071 | 4/1972 | Bergmeyer et al. | 435/193 |
| 3,749,668 | 7/1973 | Walker | 210/37 |
| 4,204,989 | 5/1980 | McAleer et al. | 530/387 |
| 4,309,339 | 1/1982 | Haupt et al. | 530/392 |
| 4,325,866 | 4/1982 | Bohn | 530/387 |
| 4,677,196 | 6/1987 | Rausch et al. | 530/412 |
| 4,693,828 | 9/1987 | Yoshika et al. | 210/679 |
| 4,740,304 | 4/1988 | Tjerneld et al. | 210/639 |
| 4,761,472 | 8/1988 | Schultze | 540/145 |
| 4,771,104 | 9/1988 | Kodama et al. | 525/54.1 |
| 4,771,128 | 9/1988 | Ferris et al. | 530/417 |
| 4,778,813 | 10/1988 | Fenyes et al. | 514/357 |

FOREIGN PATENT DOCUMENTS 2156355 10/1985 United Kingdom .

OTHER PUBLICATIONS

*Kirk-Othmer Encyclopedia of Chemical Technology*, vol. 19, p. 531.
*The Merck Index*, 1989, Budavari et al. (eds.), Merck & Co. Inc., Rahway, N.J. p. 1429.
Chemical Abstracts No. 105:62693y of NL 84 01, 963, 16 Jan. 1986.
Chemical Abstracts No. 28119x of Aoki et al. 1970 Yukagaku 19(10):972-978.

*Primary Examiner*—Margaret Moskowitz
*Assistant Examiner*—Keith C. Furman
*Attorney, Agent, or Firm*—Wendell Ray Guffey; Thomas L. Farquer

[57] ABSTRACT

A method for recovering a recombinant protein from a protein solution containing high molecular weight containing proteins by directly adding amine or quaternary ammonium compounds to the solution in amounts sufficient to selectively precipitate the high molecular weight protein contaminants.

The high molecular weight precipitates are removed and the solution is further processed to remove low molecular weight contaminating proteins and other non-protein contaminants. The recombinant protein is subsequently recovered and further processed to produce a protein composition suitable for its intended use.

6 Claims, 2 Drawing Sheets

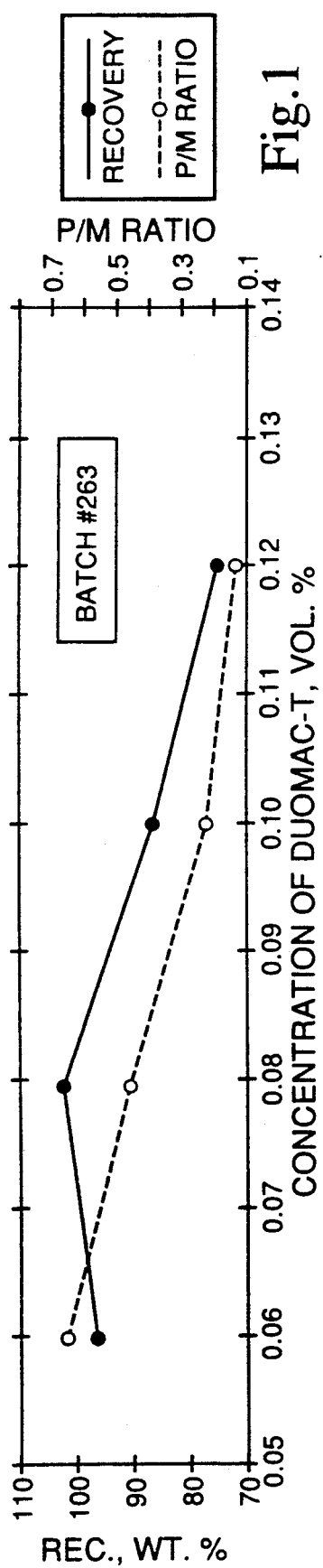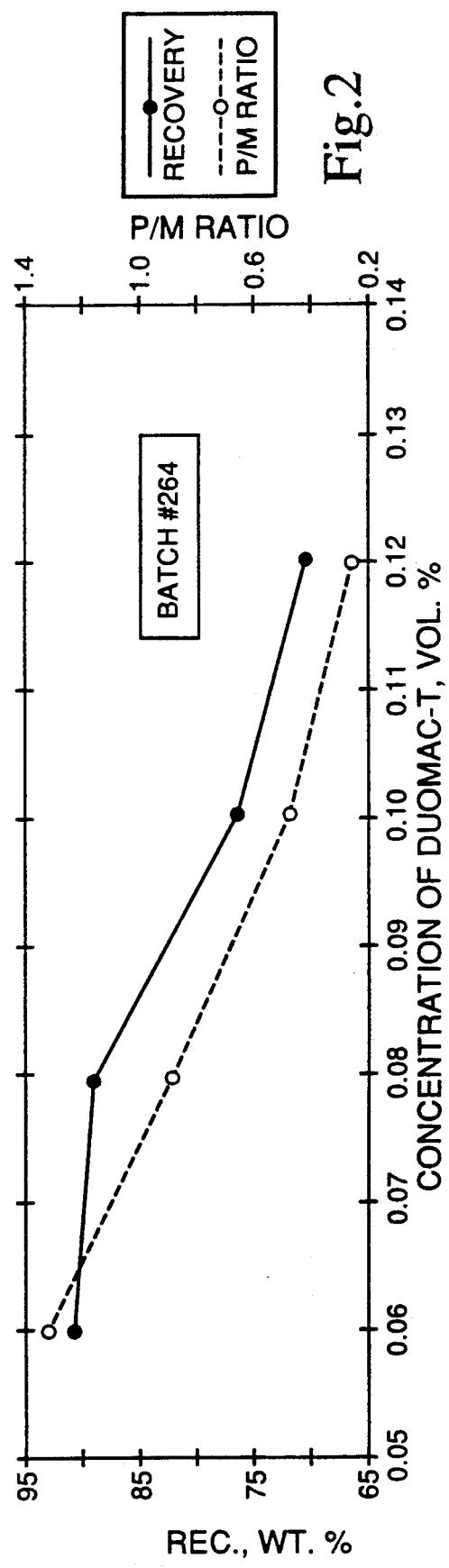

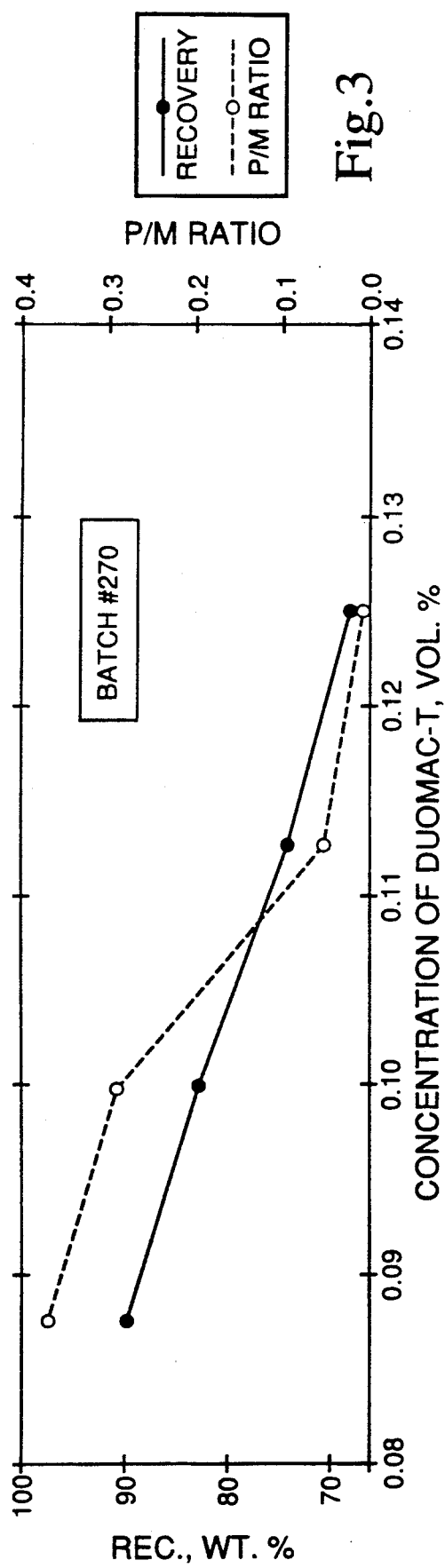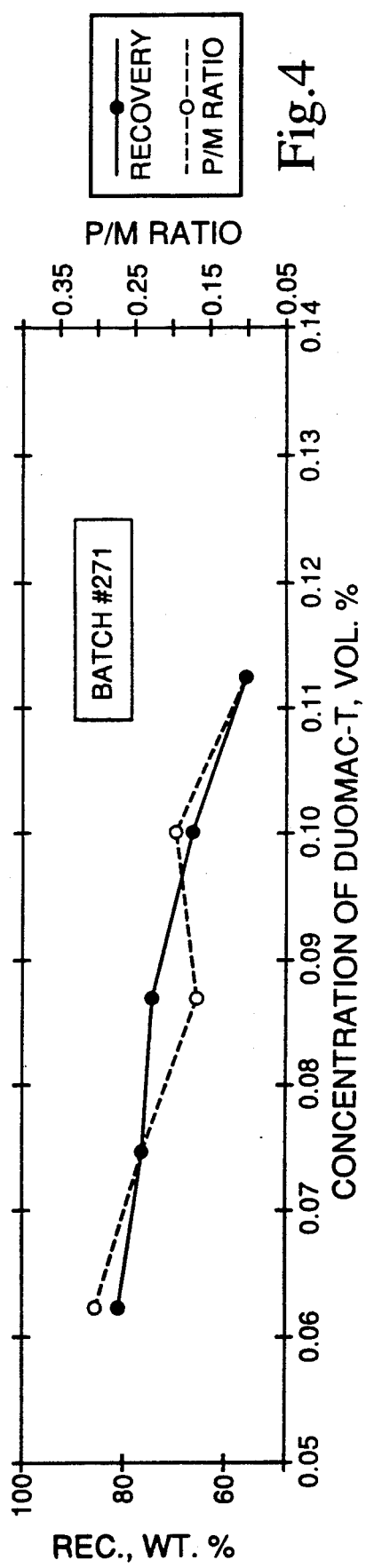

METHOD FOR RECOVERING RECOMBINANT PROTEINS

This invention relates generally to methods for recovering recombinant proteins and particularly to a method for recovering recombinant proteins from protein solutions containing high molecular weight contaminating proteins.

BACKGROUND OF THE INVENTION

Methods for producing recombinant proteins are well known in the art; heterologous DNA segments that encode for a particular protein are inserted into host microorganisms using recombinant DNA technology. By growing the transformant microorganisms under conditions which induce the expression of proteins, heterologous proteins such as insulin, somatotropins, interleukins, interferons, somatomedins, and the like can be produced.

Unfortunately, heterologous proteins produced by transformant microorganisms are frequently not biologically active because they do not fold into the proper tertiary structure when transcribed within the microorganism. The heterologous proteins tend to form aggregates which are recognizable within the cell as "inclusion bodies". These inclusion bodies may also be caused by the formation of covalent intermolecular disulfide bonds which link together several protein molecules to form insoluble complexes. The inclusion bodies generally contain mostly heterologous proteins and a small fraction of contaminating host microorganism proteins.

Several processes have been developed to extract the inclusion bodies from the microorganisms and convert the heterologous proteins contained therein into proteins having native bioactivity consistent with the natural parent or non-recombinant proteins. These processes generally involve disrupting the microorganism cell, separating the inclusion bodies from cell debris, solubilizing the inclusion body proteins in a denaturant/detergent which unfolds the protein, separating the heterologous inclusion body proteins from insoluble contaminants, removing the denaturant/detergent thereby allowing the heterologous proteins to refold into a bioactive tertiary conformation, and separating the protein from the contaminating proteins that remain in solution.

Several recombinant protein purification schemes following this general procedure are known in the art: U.S. Pat. Nos. 4,511,503 and 4,518,526 to Olson et al and U.S. Pat. Nos. 4,511,502 and 4,620,948 to Builder et al disclose multi-step methods wherein (1) inclusion bodies are solubilized in a strong denaturant and a reducing agent, (2) insoluble contaminants are removed from the solubilized protein solution, (3) the strong denaturant is replaced with a weak denaturant, (4) the protein is allowed to refold assisted by oxidation of the sulfhydryl groups to disulfide bonds using molecular oxygen and a catalyst, typically metal cations or sodium tetrathionate, and (5) the protein is separated from other contaminating proteins by membrane separation techniques or chromatography procedures.

Rausch et al., U.S. Pat. No. 4,677,196, incorporated herein by reference, discloses a particular method for purifying and activating proteins which is a variation of the general scheme described above. The method comprises solubilizing the inclusion bodies in SDS, removing the excess SDS from the solution using dialysis or other suitable technique, chromatographing the SDS-protein solution on an ion-retardation resin, and chromatographing the resulting solution on an anion-exchange resin to recover the protein.

All these known procedures share a common problem. The protein solution produced when the denaturant/detergent is removed contains the recombinant protein, low molecular weight contaminating proteins, non-protein contaminants, and high molecular weight contaminating proteins; the high molecular weight protein contaminants are often mostly dimers, oligomers and aggregates of the recombinant protein but also include non-recombinant proteins from the cell digest. It is often difficult, time consuming, and expensive to separate the recombinant protein from these contaminants, particularly the recombinant protein dimers, oligomers and aggregates. Chromatographic and membrane separation techniques may be effective for separating the recombinant proteins from the contaminants but are cumbersome, lengthy, expensive and often give low percentage yields for protein recovery.

New and improved methods for easily, quickly, and inexpensively recovering high yields of recombinant proteins from solutions containing high molecular weight protein contaminants are therefore needed.

DESCRIPTION OF DRAWINGS

FIGS. 1 through 4 are graphic representations showing the effect of DUOMAC-T concentration on porcine somatotropin recovery and polymer to monomer (P/M) ratio as determined by Gel Permeation Chromatography (GPC), for Batches 263, 264, 270 and 271, respectively.

SUMMARY OF THE INVENTION

It is, therefore, an object of the present invention to provide a new method for easily, quickly, and inexpensively recovering high yields of recombinant proteins from protein solutions containing high molecular weight contaminating proteins.

It is another object of the present invention to provide a method for removing high molecular weight contaminating proteins from a recombinant protein solution thereby allowing the easy, quick, and inexpensive recovery of the recombinant protein.

These and other objects are achieved by directly adding amine or quaternary ammonium compounds to solutions containing high molecular weight contaminating proteins and a recombinant protein in amounts sufficient to selectively precipitate the high molecular weight protein contaminants. The compounds induce preferential precipitation of proteins having a molecular weight greater than about 1.5 times the molecular weight of the recombinant protein, particularly recombinant protein dimers, oligomers and aggregates having a molecular weight greater than about 1.5 times the molecular weight of the recombinant protein. The precipitates are separated from the solution leaving the recombinant protein, low molecular weight contaminating proteins and other non-protein contaminants in solution. The recombinant protein is recovered from the solution using known techniques and processed to produce the desired protein product.

In the preferred embodiment, the amine or quaternary ammonium compound is added directly to the solution in amounts sufficient to produce a 0.01-2% solution by volume. The high molecular weight contaminating proteins precipitate and are removed from the solution by conventional means such as filtration, centrifugation, and the like. The resulting protein solution containing the recombinant protein, low molecular weight contaminating proteins and other non-protein contaminants is further processed using conventional techniques such as chromatography to recover the recombinant protein.

Other objects, advantages, and novel features of the present invention will become apparent from the following detailed description of the invention.

DETAILED DESCRIPTION OF THE INVENTION

The term "recombinant protein" as used herein defines a protein which one desires to recover in a relatively pure form and includes proteins having the amino acid sequence of native proteins and their analogs and muteins having substituted, deleted, replaced, or otherwise modified sequences.

The term "recombinant somatotropin" (rST) as used herein includes recombinant proteins having the amino acid sequence of native somatotropin, amino acid sequences substantially similar thereto, or an abbreviated sequence form thereof, and their analogs and muteins having substituted, deleted, replaced, or otherwise modified sequences. In particular, rST as used herein includes a protein of the same sequence as pST, but having amino acids deleted from its amino terminal end. Examples of such proteins include but are not limited to delta-7 recombinant porcine somatotropin, delta-4 recombinant bovine somatotropin, and the like.

The term "high molecular weight contaminating proteins" or "high molecular weight protein contaminants" as used herein refers to proteins having a molecular weight greater than about 1.5 times the molecular weight of the recombinant protein, particularly recombinant protein dimers, oligomers and aggregates having a molecular weight greater than about 2 times the molecular weight of the recombinant protein.

The term "low molecular weight contaminating proteins" or "low molecular weight protein contaminants" as used herein refers to proteins having a molecular weight less than about 1.5 times the molecular weight of the recombinant protein.

The term "non-protein contaminants" as used herein refers to relatively low molecular weight substances such as precipitating agents, solubilizing agents, oxidizing agents, reducing agents, and the like which are typically in a protein solution.

According to the present invention, a method is provided for recovering a recombinant protein from a protein solution containing high molecular weight contaminating proteins. The method comprises directly adding amine or quaternary ammonium compounds to the solution containing high molecular weight contaminating proteins and the recombinant protein in amounts sufficient to selectively precipitate the high molecular weight protein contaminants. The amine or quaternary ammonium compounds preferentially induce the precipitation of proteins having a molecular weight greater than about 1.5 times the molecular weight of the recombinant protein, particularly recombinant protein dimers, oligomers and aggregates having a molecular weight greater than about 2 times the molecular weight of the recombinant protein. The method provides an improved method for easily, quickly, and inexpensively recovering high yields of recombinant proteins from solutions containing high molecular weight protein contaminants.

In the preferred embodiment, a method is provided for recovering recombinant somatotropins (molecular weight about 20,000) by directly adding amine or quaternary ammonium compounds to solutions containing high molecular weight contaminating proteins and recombinant somatotropins in amounts sufficient to selectively precipitate the high molecular weight protein contaminants. The amine or quaternary ammonium compounds preferentially induce the precipitation of proteins having a molecular weight greater than about 1.5 times the molecular weight of the recombinant somatotropin (molecular weight greater than about 30,000), particularly recombinant somatotropin dimers, oligomers and aggregates having a molecular weight greater than about 2 times the molecular weight of the recombinant somatotropin (molecular weight about 40,000 and up). The present method, therefore, provides a method for separating the recombinant somatotropin from its bioinactive dimers, oligomers and aggregates.

Solutions containing a recombinant protein, non-protein contaminants, high molecular weight protein contaminants, and low molecular weight protein contaminants useful in the present invention are obtained by methods known in the art. Typically, protein inclusion bodies which have been produced by recombinant microorganisms are processed to remove lipids, and cell debris and the resulting relatively pure inclusion bodies containing recombinant protein and contaminating proteins, particularly high molecular weight recombinant protein dimers, oligomers and aggregates, are solubilized in a strong denaturant or detergent such as guanidine hydrochloride, sodium dodecyl sulfate (SDS), Triton, and the like.

The resulting protein solution is separated from any insoluble materials and the strong denaturant or detergent is removed to produce a protein solution containing the recombinant protein refolded into its native bioactive configuration, high molecular weight protein contaminants, low molecular weight contaminating proteins and other non-protein contaminants. Such solutions typically contain from about 1-50 mg/ml total protein and from about 0.05-4 mg/ml recombinant protein.

The amine or quaternary ammonium compounds are added to this solution according to the present invention to precipitate the high molecular weight contaminating proteins.

The high molecular weight contaminating proteins that precipitate upon addition of the amine or quaternary ammonium compounds are removed from the solution by conventional means such as filtration, centrifugation, and the like. The resulting protein solution containing the recombinant protein, low molecular weight contaminating proteins and other non-protein contaminants, if any, is further processed, as needed, to remove low molecular weight contaminating proteins and other non-protein contaminants such as precipitating agents, solubilizing agents, oxidizing agents, reducing agents, and the like. Typically, such non-protein contaminants are removed by dialysis, chromatography, or other suitable means whereas the low molecular weight contaminating proteins are separated from the protein by ion-exchange or other forms of chromatography.

The protein solution is further processed to produce a protein or protein composition suitable for its intended use, typically by lyophilization. These methods are well known in the art.

Amine or quaternary ammonium compound useful in the present invention are selected from compounds having the structure:

wherein $R_1$, $R_2$, $R_3$ and $R_4$, which may be same or different, are selected from the group consisting of straight or branched $C_8$–$C_{20}$ alkyl, straight or branched $C_8$–$C_{20}$ substituted alkyl and hydrogen, provided at least one among $R_1$, $R_2$, $R_3$ and $R_4$ is not hydrogen; and X is an anion such as chloride, bromide, iodide, sulfate, sulfonate, nitrate, acetate and the like; or

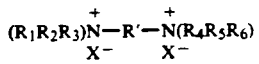

wherein $R_1$ is selected from the group consisting of straight or branched $C_8$–$C_{20}$ alkyl, straight or branched $C_8$–$C_{20}$ substituted alkyl; $R_2$–$R_6$ are selected from the group consisting of straight or branched $C_8$–$C_{20}$ alkyl, straight or branched $C_8$–$C_{20}$ substituted alkyl and hydrogen; R' is an alkylene or arylene group; and X is an anion such as chloride, bromide, iodide, sulfate, sulfonate, nitrate, acetate and the like; or

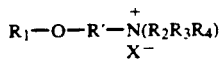

wherein $R_1$, $R_2$, $R_3$ and $R_4$, which may be the same or different are selected from the group consisting of straight or branched $C_8$–$C_{20}$ alkyl, straight or branched $C_8$–$C_{20}$ substituted alkyl and hydrogen, provided at least one among $R_1$, $R_2$, $R_3$ and $R_4$ is not hydrogen; R' is an alkylene or arylene group; and X is an anion such as chloride, bromide, iodide, sulfate, sulfonate, nitrate, acetate and the like; or

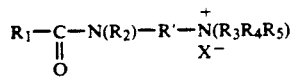

wherein $R_1$, $R_2$, $R_3$, $R_4$ and $R_5$, which may be the same or different, are selected from the group consisting of straight or branched $C_8$–$C_{20}$ alkyl, straight or branched $C_8$–$C_{20}$ substituted alkyl or hydrogen, provided at least one among $R_1$, $R_2$, $R_3$ and $R_4$ is not hydrogen; and X is an anion such as chloride, bromide, iodide, sulfate, sulfonate, nitrate, acetate and the like; or

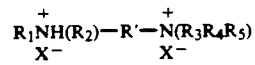

wherein $R_1$ is a group derived from Tallow; $R_2$, $R_3$, $R_4$ and $R_5$, which may be same or different are selected from the group consisting of straight or branched $C_8$–$C_{20}$ alkyl, straight or branched $C_8$–$C_{20}$ substituted alkyl or hydrogen; R' is an alkylene or arylene group; and X is an anion such as chloride, bromide, iodide, sulfate, sulfonate, nitrate, acetate and the like.

Preferred compounds include dodecylamine hydrochloride, trimethyloctadecyl ammonium chloride, trimethylhexadecyl ammonium chloride, trimethyldodecyl ammonium chloride, dimethyldiammonium chloride and DUOMAC-T (N-tallow-1, 3-diaminopropane diacetate). Most preferred compounds include DUOMAC-T (N-tallow-1,3-diaminopropane diacetate) and trimethyl dodecyl ammonium chloride.

Although the amount of amine or quaternary ammonium compound needed to induce precipitation varies depending on protein concentration, protein characteristics, compound added, and the like, the amine or quaternary ammonium compounds are typically added to the solution in amounts sufficient to produce from about a 0.01–2% by volume solution of the compound, preferably from about a 0.01–0.5% solution by volume.

Recombinant proteins recoverable using the method of the present invention can be any protein having a molecular weight greater than about 5000 which are produced by recombinant microorganisms, typically in inclusion bodies. These include somatotropins, insulins, somatomedins, somatostatins, prolactins, placental lactogens, and the like.

Most preferably, recombinant somatotropins (molecular weight about 20,000) are recovered using the method of the present invention. The recombinant somatotropin can be a recombinant somatotropin from any species but are preferably bovine, porcine, avian, ovine, or human recombinant somatotropin, most preferably porcine or bovine recombinant somatotropin.

Methods for producing these recombinant proteins are well known in the art: For example, U.S. Pat. Nos. 4,604,359 and 4,332,717 disclose methods for producing human recombinant somatotropin; U.S. Pat. No. 4,431,739 discloses a method for producing recombinant somatotropins; E.P. Patent Application 0 104 920 discloses a method for producing recombinant porcine somatotropin; U.S. Pat. No. 4,443,359 discloses a method for producing recombinant bovine somatotropin; Schoner, *Biotechnology*, 3(2):151-54, discloses a method for producing recombinant somatotropin, and Buell, *Nucleic Acid Res.*, 13, 1923-38 (1985) discloses a method for producing recombinant somatomedin C.

Also, European Patent Application Publication No. 0 103 395 describes the construction of a transformant strain of *E. coli* containing a first plasmid which codes for delta 9 (Ser) bovine somatotropin (somatotropin less its 9 N-terminal amino acids and having an additional serine residue at the N-terminus) under the control of the lambda P L promoter-operator and which has a Shine-Dalgarno region derived from bacteriophage mu. The transformant also contains a second plasmid, pcI857, which codes for the production of the pcI857 temperature-sensitive repressor protein. The repressor protein can be inactivated by raising the temperature to about 42° C., thereby inducing expression of delta 9 (Ser) bovine somatotropin. A transformant strain of this type, *E. coli* HB101 (P L-mu-delta 9 (Ser) bovine somatotropin and pcI857) has been deposited, with The American Type Culture Collection (ATCC), Rockville, Md. and assigned Accession No. 53030.

Construction of a similar transformant strain which codes for the production of delta 7 porcine somatotropin (porcine somatotropin less its first 7 N-terminal amino acids) is described in European Patent Application Publication No. 0 104 920. A transformant strain of this type, *E. coli* HB101 (P L-mu-delta 7 porcine somatotropin and pcI857) has been deposited with ATCC and assigned Accession No. 53031.

Strains 53030 and 53031 are prolific producers of delta 9 (Ser) bovine somatotropin and delta 7 porcine somatotropin, respectively. In both instances, the expressed protein is sequestered within the cell in the form of insoluble, biologically inactive inclusion bodies which are visible under a microscope. Other methods for many similar proteins are known in the art.

In the preferred embodiment, a recombinant somatotropin solution containing from about 1–50 mg/ml total protein and from about 0.05–2 mg/ml recombinant somatotropin is treated with from about 0.08–0.12% DUOMAC-T to precipitate the high molecular weight protein contaminants. The precipitate is removed by centrifugation and the recombinant somatotropin is recovered from the resulting solution using conventional means as described above.

Although the above recovery method is directed to recovering recombinant proteins, the method is equally applicable to separating and recovering non-recombinant proteins. For example, a solution containing a mixture of (1) a "useful or wanted protein", (2) high molecular weight proteins (molecular weight greater than about 1.5 times the molecular weight of the useful protein) and (3) low molecular weight proteins (molecular weight less than about 1.5 times the molecular weight of the useful protein) is treated according to the present invention to precipitate the high molecular weight proteins and thus separate the high molecular weight proteins from the useful protein and the low molecular weight proteins. The high molecular weight proteins are separated from the solution and discarded or further processed, as desired; the high molecular weight proteins can be recovered from the precipitate by redissolving the precipitate and recovering the proteins from the solution.

The useful protein is separated from the low molecular weight proteins by conventional means and further processed, if desired, to produce a protein product. The low molecular weight proteins which were separated from the useful protein are discarded or further processed, as desired. Typically, the low molecular weight proteins can be separated from the useful protein by chromatography or other means suitable for separating proteins having similar molecular weights. Many such protein separation means are well known to skilled artisans and are equally applicable in the present invention.

The invention having been generally described, the following examples are given as particular embodiments of the invention and to demonstrate the practice and advantages thereof. It is understood that the examples are given by way of illustration and are not intended to limit the specification or the claims to follow in any manner. In particular, inclusion bodies used in the experiments were prepared from transformed E. Coli strains which produce delta-7 porcine somatotropin. The inclusion bodies were isolated from E. Coli host strain HB101 transformed with a first plasmid (pL-mu-delta-7 pST) coding for delta-7 pST and a second plasmid (pcI857) coding for the temperature sensitive lambda phage repression protein. Many other strains of microorganisms produce inclusion bodies containing many types of recombinant proteins which will function in the present invention. Similarly, methods for growing these microorganisms to produce inclusion bodies are well known in the art.

EXAMPLE 1

Recombinant porcine somatotropin (rpST) was recovered from microorganism inclusion bodies by (1) dissolving the inclusion bodies in sodium dodecyl sulfate (SDS), (2) removing insoluble contaminants from the solution, and (3) removing the SDS from the solution to allow the rpST to refold into its bioactive configuration. The resulting protein solution contained the rpST, high molecular weight protein contaminants, low molecular weight contaminating proteins and other non-protein contaminants. This solution was subjected to a membrane separation process for purification. The membrane separation removed some high molecular weight impurities but a significant amount of high molecular weight impurities remained; further purification was needed.

20 Milliliter (ml) samples of the protein solution containing the rpST high molecular weight protein contaminants, low molecular weight contaminating proteins and other non-protein contaminants were added to 50 ml beakers which were placed in an ice filled tub to keep the temperature between 5°–10° C. A predetermined amount of a 0.5–1.0% solution of the amine reagent (dodecylamine hydrochloride, A-1 and A36A amine compounds) was added to the sample using a 1 ml or 3 ml syringe. Reactants in each beaker were gently mixed using a Teflon coated stirring bar for about 1–3 minutes. Precipitates formed almost immediately; slower rate of addition (dropwise) of the pricipitant gave a purer product (lower P/M ratio). Likewise, higher temperature (25° C.) yielded higher recovery. (However, in actual practice, operation at higher temperature may not be feasible because of concerns regarding microbial growth). Contents of each beaker were centrifuged and supernatant was filtered through a 0.2 micron filter to prepare the sample for the gel permeation chromatography (GPC).

Overnight storage of the centrifuged supernatant did not show any precipitation indicating that the reaction was complete. The supernatant was analyzed using GPC and the data was then used to calculate the rpST recovery and the polymer to monomer (P/M) ratio in the supernatant product.

The results indicate that pST recoveries of about 90% with almost zero P/M ratio were obtained with about 0.05% (by volume of liquid) concentration of the amine reagent. Commercial amine compounds P-14B and 52-267 were also tested but discarded in favor of dodecylamine hydrochloride and A-1 because of either lower recovery, higher P/M ratio or the dosage required.

EXAMPLE 2

Selected amine compounds A-1 and dodecyl amine hydrochloride from Example 1 and several others including trimethyl dodecyl-, hexadecyl- and octadecyl ammonium chlorides, DUOMAC-T (N-tallow- 1,3-diaminopropane diacetate), ARQUAD-2C-75 (dimethyldicoco ammonium chloride) and hexylamine were tested at different concentrations on several pilot-plant samples which had not been subjected to membrane purification. Except hexylamine, each one of the above reagents resulted in protein precipitation. However, the selectivity and pST recovery varied.

Among dodecyl-, hexadecyl- and octadecyl ammonium chlorides, concentration of the reagent required to selectively precipitate pST polymer was a function of carbon chain length in that 18 carbon octadecyl compound required only 0.02% (by volume of solution) as opposed to 0.03% for 16 carbon hexadecyl and about 0.04–0.06% for the 12 carbon dodecyl compound. At the same P/M ratio in the product, pST recovery was the highest with trimethyl dodecyl ammonium chloride (TDAC).

Of all the amine compounds tested, DUOMAC-T in the concentration range between 0.08–0.12% appeared to be the most promising in terms of selectivity and recovery.

Table 2 presents a summary of precipitation test data obtained using DUOMAC-T and TDAC with different batches of recombinant protein. The recoveries (75–82%) are better than the recoveries for membrane purification techniques. In addition, the precipitation process of the present invention is much simpler and trouble free. Since the products are usually very valuable, small improvements in recovery produce large economic benefits.

The effect of DUOMAC-T concentration on pST recovery and P/M ratio was investigated in detail for several other batches of crude recombinant protein. As some typical results presented in FIGS. 1 through 4 show, there is a trade off between pST recovery and P/M ratio i.e. higher recovery is associated with higher P/M ratio. Since a desired P/M ratio in the prepurified product is about 0.5 or less, DUOMAC-T concentration should be selected to meet this condition with the highest possible recovery.

pST supernatant obtained after the DUOMAC-T precipitation was analyzed by the tissue binding assay, Isoelectric Focusing (IEF) and High Pressure Liquid Chromatography (HPLC). Tissue binding assay showed pST to be 98% active with respect to a standard pST sample suggesting that pST was not denatured. Likewise, the IEF and HPLC tests did not show any difference between the DUOMAC-T treated and untreated pST samples indicating unchanged pST structure.

Obviously many modifications and variations of the present invention are possible in light of the above teachings. It is therefore to be understood that within the scope of the appended claims the invention may be practiced otherwise than as specifically described.

TABLE 1

| List of Reagents Tested for Selective Precipitation of pST Polymer | |
|---|---|
| Reagent | Supplier |
| Hexylamine | Aldrich Chemical Co., Inc., Milwaukee, WI |
| Dodecylamine hydrochloride | Eastman Kodak, Rochester, NY |
| Trimethyloctadecyl-ammonium chloride | ARMAC Chemicals, McCook, IL |
| Trimethylhexadecyl-ammonium chloride | Eastman Kodak, Rochester, NY |
| Trimethyldoecyl-ammonium chloride | ARMAC Chemicals, McCook, IL |
| Dimethyldicoco-ammonium chloride | ARMAC Chemicals, McCook, IL |
| Dimethyldiammonium chloride | ARMAC Chemicals, McCook, IL |
| N-Tallow-1-3-diaminopropane diacetate (DUOMAC-T) | ARMAC Chemicals, McCook, IL |
| A-1 Amine P-14B, A-36A, 52-267* | Sherex Polymer, Inc., Lakeland, FL |

*All Commercial Products:
A-1: Acetate salt of a primary amine. Secondary and tertiary amine components may be present as impurity.
P-14B: $C_{10}H_{21}$—O—$CH_2$—$CH_2$—$NH_2$: Etheramine acetate.
A-36A: Fatty acid amido amine's acetate salt
52-26F: 5% Aqueous dispersion of the amine used A-36A.

TABLE 2

Recovery and P/M Ratio obtained by the Amine Process in the Treatment of Porcine Somatotropin Prepurification Feed from Different Pilot-Plant Batches

| Feed | Wt % Recovery | P/M Ratio |
|---|---|---|
| Batch #263-6 (538 ppm, 2.3 P/M) | | |
| Dodecylamine hydrochloride (0.06%) | 77 | 0.7 |
| DUOMAC-T (0.1%) | 86 | 0.15 |
| Batch #264-6 (672 ppm, 2.1 P/M) | | |
| TDAC (0.05%) | 62 | — |
| DUOMAC-T (0.1%) | 76 | 0.5* |
| Batch #265-6 (660 ppm, 2.5 P/M) | | |
| TDAC ((0.03%) | 77 | 0.2 |
| DUOMAC-T (0.075%) | 83 | 0.3–0.5 |
| DUOMAC-T (0.1%) | 79 | 0.1–0.3 |
| Batch #266-6 (610 ppm, 3.6 P/M) | | |
| TDAC (0.03%) | 75 | 0.6 |
| DUOMAC-T (0.1%) | 85 | 0.6 |
| Batch #270-6 (606 ppm, 3.9 P/M) | | |
| TDAC (0.05%) | 85 | 0.67 |
| DUOMAC-T (0.09%) | 89 | 0.35 |
| DUOMAC-T (0.11%) | 73 | 0.05 |
| Batch #271-6 (369 ppm, 3.9 P/M) DUOMAC-T (0.06%) | 82 | 0.3 |
| Batch #273-6 (369 ppm, 4.0 P/M) DUOMAC-T (0.075%) | 76 | 0.4 |
| Batch #279-6 (416 ppm, 3.2 P/M) DUOMAC-T (0.05%) | 88 | 0.6 |
| Batch #280-6 (295 ppm, 4.2 P/M) DUOMAC-T (0.06%) | 82 | 0.5 |
| Batch #268-OOE (682 ppm, 6.1 P/M) DUOMAC-T (0.15%) | 85 | 0.3 |
| AVERAGE | | |
| TDAC | 75 | 0.4 |
| DUOMAC-T | 82 | 0.4 |

*Suspect interference from a trailing peak of the previous sample.

What is claimed is:

1. A method for recovering recombinant somatotropin from a protein solution containing high molecular weight contaminating proteins, those proteins having a molecular weight greater than about 1.5 times the molecular weight of the recombinant somatotropin, and the recombinant somatotropin, comprising:
    directly adding amine or quaternary ammonium compounds selected from the group consisting of dodecylamine hydrochloride, trimethyloctadecyl ammonium chloride, trimethylhexadecyl ammonium chloride, trimethyldodecyl ammonium chloride, trimethyldicoco ammonium chloride, dimethyldiammonium chloride, N-tallow-1, 3-diaminopropane diacetate and dimethyldicoco ammonium chloride to the solution in amounts sufficient to selectively precipitate the high molecular weight contaminating proteins;
    separating the precipitate from the solution; and
    recovering the recombinant somatotropin from the solution.

2. The method of claim 1 wherein the amine or quaternary ammonium compound is selected from the group consisting of N-tallow-1,3-diaminopropane diacetate and trimethyl dodecyl ammonium chloride.

3. The method of claim 1 wherein the total somatotropin concentration of the solution is from about 1–50 mg/ml and the recombinant somatotropin concentration of the solution is from about 0.05–4 mg/ml.

4. The method of claim 1 wherein the amine or quaternary ammonium compound is added directly to the solution in amounts sufficient to produce a 0.01–2% solution by volume.

5. The method of claim 1 wherein the recombinant somatotropin is bovine, porcine, avian, ovine or human recombinant somatotropin.

6. The method of claim 5 wherein the recombinant somatotropin is porcine or bovine recombinant somatotropin.

* * * * *

UNITED STATES PATENT AND TRADEMARK OFFICE
CERTIFICATE OF CORRECTION

PATENT NO. : 5,101,018
DATED : March 31, 1992
INVENTOR(S) : Mehrotra et al

It is certified that error appears in the above-identified patent and that said Letters Patent is hereby corrected as shown below:

In the Abstract, lines 2 and 3, "con-taining" should read --contaminating--

Column 9, Table 1 footnotes, line 66,

"P-14 B: $C_{10}H_{21}-O-CH_2-CH_2-NH_2$: Etheramine acetate"

should read

--P-14B: $C_{10}H_{21}-O-CH_2-CH_2-CH_2-NH_2$: Etheramine acetate--

Signed and Sealed this

Twenty-second Day of June, 1993

Attest:

MICHAEL K. KIRK

Attesting Officer

Acting Commissioner of Patents and Trademarks